(12) United States Patent
Taufiq-Yap et al.

(10) Patent No.: US 8,298,981 B2
(45) Date of Patent: Oct. 30, 2012

(54) PROCESS TO PRODUCE HIGH SURFACE AREA NANOPARTICLE VANADIUM PHOSPHORUS OXIDE CATALYST AND PRODUCT DERIVES THEREOF

(75) Inventors: Yun Hin Taufiq-Yap, Selangor (MY); Ali Asghar Rownaghi, Selangor (MY)

(73) Assignee: Universiti Putra Malaysia, Selangor (MY)

( * ) Notice: Subject to any disclaimer, the term of this patent is extended or adjusted under 35 U.S.C. 154(b) by 85 days.

(21) Appl. No.: 12/740,071

(22) PCT Filed: Apr. 14, 2008

(86) PCT No.: PCT/MY2008/000032
§ 371 (c)(1), (2), (4) Date: Aug. 24, 2010

(87) PCT Pub. No.: WO2009/061167
PCT Pub. Date: May 14, 2009

(65) Prior Publication Data
US 2010/0311574 A1    Dec. 9, 2010

(30) Foreign Application Priority Data
Nov. 9, 2007  (MY) ................................ PI20071948

(51) Int. Cl.
*B01J 27/25* (2006.01)
*B01J 37/34* (2006.01)
*B01J 27/00* (2006.01)
*B01J 27/198* (2006.01)

(52) U.S. Cl. ............. 502/201; 502/5; 502/208; 502/209

(58) Field of Classification Search .............. 502/5, 201, 502/208, 209
See application file for complete search history.

(56) References Cited

U.S. PATENT DOCUMENTS

| | | | |
|---|---|---|---|
| 4,132,670 A | 1/1979 | Katsumoto et al. | |
| 4,187,235 A | 2/1980 | Katsumoto et al. | |
| 4,209,423 A * | 6/1980 | Hutchings et al. | 502/209 |
| 4,333,853 A | 6/1982 | Milberger et al. | |
| 4,360,453 A | 11/1982 | Lemanski et al. | |
| 4,392,986 A * | 7/1983 | Yang et al. | 502/209 |
| 4,562,268 A | 12/1985 | Wrobleski et al. | |
| 4,569,925 A | 2/1986 | Yang et al. | |
| 5,530,144 A | 6/1996 | Tsurita et al. | |
| 5,932,746 A * | 8/1999 | Herron et al. | 549/260 |
| 6,228,798 B1 * | 5/2001 | Sookraj | 502/209 |
| 6,652,823 B2 * | 11/2003 | Teunissen | 423/308 |
| 7,060,649 B2 | 6/2006 | Weiguny et al. | |
| 7,169,732 B2 | 1/2007 | Weiguny et al. | |
| 7,638,457 B2 * | 12/2009 | Ghelfi et al. | 502/209 |

* cited by examiner

*Primary Examiner* — Patricia L Hailey
(74) *Attorney, Agent, or Firm* — Preston Smirman; Smirman IP Law, PLLC

(57) ABSTRACT

An improved process to produce high surface area nanoparticle vanadium phosphorus oxide catalysts comprises the steps of reducing vanadium-containing compounds in an alcohol solution selected from the group consisting of isobutanol and benzyl alcohol and any combination derives thereof under reflux for 4 to 6 hours to form a suspended mixture; reacting dopants and phosphorus-containing compounds to the suspended mixture under reflux for 30 minutes to 3 hours to form precursors of the vanadium phosphorus oxide catalysts; drying the formed precursors; and calcining the dried precursors in a flow of gaseous n-butane/air mixture at 400 to 460° C. to form activated vanadium phosphorus oxide catalysts.

18 Claims, 16 Drawing Sheets

PROCESS TO PRODUCE HIGH SURFACE AREA NANOPARTICLE VANADIUM PHOSPHORUS OXIDE CATALYST AND PRODUCT DERIVES THEREOF

CROSS-REFERENCE TO RELATED APPLICATION

The instant application claims priority to Malaysian Patent Application No: PI20071948, filed Nov. 9, 2007, pending, and PCT International Application No. PCT/MY2008/000032, filed on Apr. 14, 2008, pending, the entire specifications of both of which are expressly incorporated herein by reference.

FIELD OF INVENTION

The present invention relates to an improved process to produce nanoparticle of vanadium phosphorus oxide catalysts with high surface area. In more particular, the disclosed process is capable of producing precursors of vanadium phosphorus oxide catalyst in a much shorter time comparing to the available methods, yet the nanoparticle of vanadium phosphorus oxide catalysts derive thereof have high surface area.

BACKGROUND OF THE INVENTION

Vanadyl hydrogen phosphate hemihydrate, $VOHPO_4.0.5H_2O$, has tremendous technological importance as the precursor to the vanadyl pyrophosphate, $(VO)_2P_2O_7$ which is used as the catalysts for the commercially established selective oxidation of butane to maleic anhydride. Maleic anhydride is a commercially important chemical intermediate for acquiring unsaturated polyester, succinic anhydride, gamma-butyrolactone, 1,4-butanediol, tetrahydrofuran, fumaric acid, malic acid and d,l-tartaric acid. Vanadyl hydrogen phosphate hemihydrate is known to be crucially in determining the catalytic activity and selectivity of the produced vanadyl pyrophosphate. In fact, it is the surface area of the produced vanadyl pyrophosphate that affects the catalytic activity and selectivity because higher surface area implies higher number of active sites per unit mass of catalysts. Thus, the higher surface area catalysts can operate at lower temperatures which lead to enhance selectivity.

U.S. Pat. No. 4,333,853 is an application regarding to a method to prepare vanadium phosphorus oxide catalysts by reducing pentavalent vanadium compounds and pentavalent phosphorus compounds together under reflux. In this disclosed US application, the reflux needed to be conducted for at least 16 hours to finally acquire the vanadyl hydrogen phosphate hemihydrate and no dopant is suggested to be used to enhance the catalytic activity of the produced vanadium phosphorus oxide catalysts. Milberger et al. filed another patent application in U.S. Pat. No. 4,360,453. In this application, Milberger et al. suggested an extraction method to recover the produced catalyst precursors, vanadyl hydrogen phosphate hemihydrate, by dissolving the produced precursors into water. The dissolved precursors were then recovered via evaporation or spray drying. Moreover, this disclosed method employed gases such as HBr and HCl as the reducing agent by passing these gases through the organic media, thus no reflux of the organic media is needed in this method.

U.S. Pat. Nos. 4,132,670 and 4,187,235 disclosed another method to prepare vanadium phosphorus oxide catalysts. The disclosed method includes two different stages of reflux which at first reduces the pentavalent vanadium-containing compounds, then reflux the reduced vanadium-containing compounds with orthophosphoric compounds thus forming the catalyst precursors, vanadyl hydrogen phosphate hemihydrate. These applications have suggested in using mixture of vanadium with others rare metal in preparing the vanadium phosphorus oxide by refluxing the mixture at the first stage of reflux. In order to produce high surface area catalysts, inventors of the present application found that utilization of other metal or dopants shall be involved in second stage of reflux for a short period of time instead of as proposed by the aforementioned US applications.

On the other hand, U.S. Pat. No. 4,562,268 is another improved method to produce vanadium phosphorus oxide catalysts. This application has claimed employing an alcohol modifying agent in the reducing process which leads to production of catalysts with high surface area.

U.S. Pat. No. 4,569,925 also filed an application on reacting vanadium-containing compound with phosphorus-containing compounds in a liquid organic media to produce the precursors, and then activate the precursors to form the vanadium phosphorus oxide catalysts with a type of inert air and at least one hydrocarbon. In this US application, all the reactants are reflux in a single reaction to produce the precursor.

SUMMARY OF THE INVENTION

The present invention aims to disclose a process to produce nanoparticles of vanadium phosphorus oxide catalysts with high surface area. In more specific, the present invention employs a suitable dopant not only to increase the surface area but also increase the reactivity of the oxygen species in the catalysts.

It is object of the present invention to disclose a process to produce vanadium phosphorus oxide catalysts possessing high selectivity. Due to the high surface area, the vanadium phosphorus oxide catalysts derives from the disclosed process can operate at lower temperature in oxidizing n-butane to maleic anhydride thus the reaction can be performed at higher selectivity.

Still another object of the present invention includes providing a process to produce vanadium phosphorus oxide catalysts or its precursors, vanadyl hydrogen phosphate hemihydrate, in a short duration of reflux in contrast to the prior arts. It was found by the inventors of the present invention that reflux of reduced vanadium-containing compounds with phosphorus-containing compound and a suitable dopant for a short duration is capable of producing vanadium phosphorus oxide catalysts with high surface area from the produced precursors.

Owing to the shorter reaction time, the present invention is also capable of offering a cost-saving process to produce vanadium phosphorus oxide catalysts.

At least one of the preceding objects is met, in whole or in part, by the present invention, in which one of the embodiment of the present invention includes an improved process to produce vanadyl hydrogen phosphate hemihydrate comprises the steps of reducing vanadium-containing compounds in an alcohol solution selected from the group consisting of isobutanol, benzyl alcohol and any combination derives thereof under reflux for 4 to 6 hours phosphorus-containing compounds to the suspended mixture under reflux for 30 minutes to 3 hours to form the vanadyl hydrogen phosphate hemihydrate. According to further embodiment, the present invention may comprise the steps of recovering the formed precursors from the suspended mixture; and drying the recovered precursors.

Another embodiment of the present invention is an improved process to produce vanadium phosphorus oxide catalysts comprises the steps of reducing vanadium-containing compounds in an alcohol solution selected from the group consisting of isobutanol, benzyl alcohol and any combination derives thereof under reflux for 4 to 6 hours to form a suspended mixture; reacting dopants and phosphorus-containing compounds to the suspended mixture under reflux for 30 minutes to 3 hours to form precursors of the vanadium phosphorus oxide catalysts; drying the formed precursors; and calcining the dried precursors in a gas flow of gaseous n-butane/air mixture at 400 to 460° C. to form activated vanadium phosphorus oxide catalysts.

In respect to the preferred embodiment, the dopants employed in the present invention is any one or combination of Lanthanum (III) nitrate hexahydrate, Cerium (III) nitrate hexahydrate and Niobium Pentoxide.

In order to enhance the reactivity of the catalysts derive from the formed precursors, the drying step is preferably conducted by irradiating the formed precursor with microwave.

Still another embodiment of the present invention is the vanadium phosphorus oxide catalyst produced from the disclosed processes which is characterized in that the catalyst has can reached a surface area of more than 45 $m^2/g$.

Further embodiment of the vanadium phosphorus oxide catalyst produced from the disclosed methods can be characterized in that the catalysts has a rhomboid platelet structure with an average particle size of 10-50 nm in width and 40-60 nm in length.

DETAILED DESCRIPTION OF THE INVENTION

Figure 1:
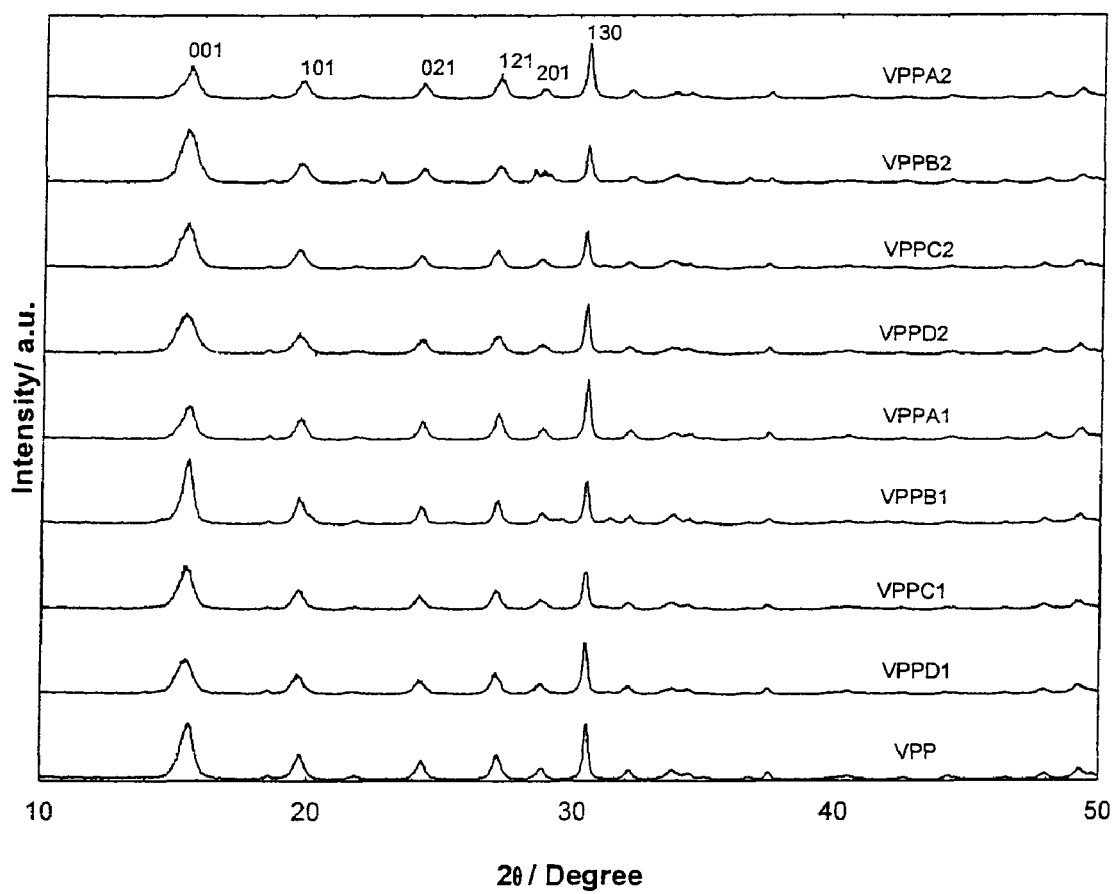
FIG. 1 shows the XRD Patterns of new and conventional VPO method for undoped and doped catalyst precursor; (001) and (130) main peaks for $VOHPO_4.0.5H_2O$.

It is to be understood that the present invention may be embodied in other specific forms and is not limited to the sole embodiment described herein. However modification and equivalents of the disclosed concepts such as those which readily occur to one skilled in the art are intended to be included within the scope of the claims which are appended thereto.

One of the embodiments of the present invention discloses an improved process to produce an intermediate precursor of vanadium phosphorus oxide catalysts, vanadyl hydrogen phosphate hemihydrate, within a short reflux period. It is important to be noted that the vanadium phosphorus oxide catalysts or vanadyl pyrophosphates $[(VO)_2P_2O_7]$ derive from the precursors produced by the disclosed process possessing high surface area as well as high selectivity. In order to produce the precursors, the preferred embodiment of the process comprises the steps of reducing vanadium-containing compound in an alcohol solution consisting of isobutanol, benzyl alcohol and any combination derives thereof under reflux for 4 to 6 hours to form a suspended mixture; and reacting dopants and phosphorus-containing compound to the suspended mixture under reflux for 30 minutes to 3 hours to form the vanadyl hydrogen phosphate hemihydrate.

In respect to the further embodiment, the vanadyl phosphate hemihydrate shall precipitate in the suspended mixture. Thus the steps of the process may further comprise recovering the formed precursors from the suspended mixture; and drying the recovered precursors for storage or use.

Attention is now drawn to another embodiment of the present invention in which the process offers production of vanadium phosphorus oxide catalysts directly from the abovementioned embodiment comprises the steps of reducing vanadium-containing compounds in an alcohol solution consisting of isobutanol, benzyl alcohol and any combination derives thereof under reflux for 4 to 6 hours to form a suspended mixture; and reacting dopants and phosphorus-containing compounds to the suspended mixture under reflux for 30 minutes to 3 hours to form precursors of the vanadium phosphorus oxide catalysts; drying the formed precursors; and calcining the dried precursors in a gas flow of n-butane and air mixture at 400 to 460° C. to form activated vanadium phosphorus oxide catalysts.

According to the set forth embodiments, representative of vanadium-containing compounds include vanadium oxides, vanadium halides, and vanadium oxyhalides. Vanadium oxides can be vanadium trioxide, vanadium trioxide and vanadium pentoxide; while vanadium halides or vanadium oxyhalides can be vanadium trichloride, vanadium tribromide, vanadyl chloride, vanadyl dichloride, vanadyl trichloride, vanadium bromide, vanadyl dibromide, and vanadyl tribromide. Moreover, either organic or inorganic vanadium salts can be used in the present invention such as ammonium metavanadate, vanadium sulfate, vanadium oxysulfate, vanadium phosphate, vanadyl formate, vanadyl oxalate and vanadyl alkoxides. Preferably, the average valence of the vanadium containing-compound is at least about +5 to +4. Nonetheless, vanadium pentoxide is most preferred.

Likewise, different phosphorus containing-compounds are suggested by the arts to form the catalysts or its precursors. Compounds such as phosphorus oxide, phosphorus halide, phosphorus oxyhalide, phosphorus salts or organophosphorus compounds are applicable in the present invention. However, phosphoric acids such as metaphosphoric acid, orthophosphoric acid, triphosphoric acid, pyrophosphoric acid or mixtures thereof are used in the most preferred embodiment. In more particular, the aqueous solution or mixtures of the phosphoric acids used in the present invention preferably have a concentration of 80%, more preferably 85%, by weight of the solution or mixture. Depending upon the types of phosphorus-containing compounds and vanadium-containing compounds, the amount of these two compounds can be varied. Preferably, ratio of the vanadium atom of the vanadium-containing compounds to the phosphorus atom of the phosphorus-containing compounds is 0.05:0.06 by mole.

As the reflux proceeds in reducing the valence of the vanadium-containing compound, water will be produced from the alcohol solution. It is important to be noted that concentration of the water produced in the alcohol solution can affect the crystalline formation of the precursor thus determine the reactivity of the vanadium phosphorus oxide catalysts derives thereof. In the preferred embodiment, the ratio of the alcohol solution to the amount of vanadium atom in the vanadium-containing compounds is preferably in the range of 20 to 40 mL/g.

Besides of using alcohol as the reducing agent, it is known in the art that other agents such as acids, organic aldehydes, hydroxylamines, hydrazine or the like are applicable in reducing the valence state of the vanadium-containing compounds. Modification by one skilled in the art from such aspects shall not depart from the scope of the present invention. Nonetheless, the reducing agent is preferably in solvent form, and the vanadium-containing compounds as well as the phosphorus-containing compounds are at lest partially soluble in this reducing solvent.

The inventor of the present invention found that incorporating suitable dopants at sufficient amount onto the crystalline structure of the precursors and the vanadium phosphorus oxide catalyst derives thereof showing high reactivity and high surface area. In accordance to the preferred embodiments, the dopants are added into the alcohol solution to react with the reduced vanadium after the first stage reflux. Nevertheless, the second stage of reflux involving both dopants and the phosphorus-containing compounds has to be conducted within a short period of time. It was found by the inventors of the present invention that prolong of the second stage reflux can greatly decrease the available surface area of the vanadium phosphorus oxide catalysts produced thus decrease also its catalytic reactivity. The types of dopants employed in the present invention, but not limited to, are Lanthanum (III) nitrate hexahydrate, Cerium (III) nitrate hexahydrate, and Niobium Pentoxide. Others dopants which may applicable in the present invention are chromium, manganese, cobalt, bismuth, antimony, tellurium, cesium and zirconium. Amount of dopants utilized preferably within in a ratio of 0.01%:0.04% to the amount of the vanadium atom of the vanadium-containing compounds used by mole. It will be noted that the exact relation between second reflux duration with dopants and available surface area of the produced catalysts is not completely understood. While not desiring to be bound by the theory of the invention or to limit the invention in anyway, it is believed that incorporation of dopants such as niobium, lanthanum, and cerium can somehow increase the surface area by decreasing the particle size to nanoscale of the catalysts and enhance release of the oxygen species from the catalyst. At present, most approaches for the synthesis of large-surface-area, high-activity catalysts make use of organic media; especially when the amount of water in solution is controlled. Water, aldehyde and ketone formed as an alcohol reduction product, but their amount can control by extractive distillation during the synthesis of the precursor phase. It is important to be noted that water based preparations tend to lead to low-surface area materials.

Further embodiment of the invention involves recovering the precipitates, vanadyl phosphate hemihydrate, from the suspended mixture upon completion of the second stage of reflux. One skilled in the art shall appreciate the fact that such recovering steps can be achieved by any known means in the art. For example the precipitates can be recovered by removing the solvent via evaporation or distillation, filtration, centrifugation and the like. It is filtration preferably employed in the present invention.

As foregoing description, the precursors require drying before subjecting to activation to form vanadium phosphorus oxide catalyst. Alternatively, the precursors are dried in room temperature or exposing to hot air or being placed in an oven. The drying step may be varied in terms of duration reliance upon the approach employed. Yet, the present invention also includes conducting the drying step via microwave irradiation. The microwave irradiation may take a period of 2 to 15 minutes under the frequency of 2450 MHz with variable power levels 140 to 300 W. Through appropriate irradiation, the catalyst produced shows higher reactivity as the amount of oxygen species released can be increased significantly. This may due to the effect of the irradiation on the chemical bonding of the catalysts at its active sites.

For activation of the dried precursors to acquire the vanadium phosphorus oxide catalyst with high surface area, numerous methods are available in the field. The activation can be performed at a selected elevated temperature at a suitable atmosphere, while such activation may be conducted in situ at the reactor to oxidize the targeted hydrocarbon or separately. It is known in the art that activation in air alone will greatly decrease the catalysts performance. Therefore, it is critical to activate the precursor in a gaseous atmosphere comprising air and a hydrocarbon, which is substantially absence of air alone. More preferable, the mixture of air and the hydrocarbon is non-explosive under the elevated activation temperature. It is known also the period required for activation will largely depend on the activation temperature and the atmosphere. The activation temperature in the present invention may range from 350° C. to 450° C. for duration of 2 to 8 hours. Preferred gaseous hydrocarbon mixed with the air is propane, butane and pentane, while n-butane is most preferred.

Based on the abovementioned process to produce both the precursors and catalysts, further embodiment entails the produced catalysts with average surface area more then 45 $m^2/g$.

Still another embodiment of the present invention is the vanadium phosphorus oxide catalyst produced from the disclosed processes which is characterized in that the catalyst has can reached a surface area of more than 45 $m^2/g$.

The following example is intended to further illustrate the invention, without any intent for the invention to be limited to the specific embodiments described therein.

Example 1

All of the reagents were commercially obtained and used without further purification. Nine samples were studied which were prepared under different condition, listed in Table 1 (The molar ratio of dopant/V is=0.04).

The standard ambient pressure preparations were carried out as follows:

The VPO method: $VOHPO_4 \cdot 0.5H_2O$ was prepared by reacting $V_2O_5$ with alcohols for 7 h. This mixture was refluxed with add $H_3PO_4$ and rapid stirring for 16 h before obtaining blue product. The resulting blue solid (denoted VPP) was recovered by filtration then heated for 12 h in reflux temperature. The blue solid $VOHPO_4 \cdot 0.5H_2O$ which is a valuable commercial catalyst precursor for the oxidation of n-butane to maleic anhydride.

In one embodiment of the preparation, $V_2O_5$ (5 g, Fluka) was reduced in mixture of iso-butyl alcohol (100 cm³, Merck) and benzyl alcohol (100 cm³, Merck) at 100 to 120° C. for 4 h. Then a definite amount dopant: $Nb_2O_5$, $LaN_3O_9 \cdot 6H_2O$ and $CeN_3O_9 \cdot 6H_2O$, was added into the black suspended mixture following phosphorus acid (85%). while maintaining a P:V ratio in the reaction mixture in the range of 1:1.0.7 to 1:1.1. A blue solid was got after the mixture refluxed for 4 h and separated by filtration. The catalysts prepared in this step listed in Table 1.

In another embodiment of the preparation, $V_2O_5$ (5 g, Fluka) was reduced in mixture of iso-butyl alcohol (100 cm³, Merck) and benzyl alcohol (100 cm³, Merck) at 100 to 120° C. for 6 h. Then a definite amount dopant: $Nb_2O_5$, $LaN_3O_9 \cdot 6H_2O$ and $CeN_3O_9 \cdot 6H_2O$, was added into the black suspended mixture following phosphorus acid (85%). A blue solid was got after the mixture refluxed for 2 h and separated by filtration. The catalysts prepared in this step listed in Table 1. All the dried precursors were calcined in a flow of n-butane/air mixture for 6 h at 733 K.

TABLE 1

| Precursor | Catalysts | Preparation condition |
|---|---|---|
| VPPA1 | VPOA1 | ($V_2O_5$ + iso-butanol + benzyl alcohol + Reflux 4 h) + o-$H_3PO_4$ (Reflux 4 h) |
| VPPA2 | VPOA2 | ($V_2O_5$ + iso-butanol + benzyl alcohol + Reflux 6 h) + o-$H_3PO_4$ (Reflux 2 h) |
| VPPB1 | VPOB1 | ($V_2O_5$ + iso-butanol + benzyl alcohol + Reflux 4 h) + o-$H_3PO_4$ + $Nb_2O_5$ (Reflux 4 h) |
| VPPB2 | VPOB2 | ($V_2O_5$ + iso-butanol + benzyl alcohol + Reflux 6 h) + o-$H_3PO_4$ + $Nb_2O_5$ (Reflux 2 h) |
| VPPC1 | VPOC1 | ($V_2O_5$ + iso-butanol + benzyl alcohol + Reflux 4 h) + o-$H_3PO_4$ + $LaN_3O_9 \cdot 6H_2O$ (Reflux 4 h) |
| VPPC2 | VPOC2 | ($V_2O_5$ + iso-butanol + benzyl alcohol + Reflux 6 h) + o-$H_3PO_4$ + $LaN_3O_9 \cdot 6H_2O$ (Reflux 2 h) |
| VPPD1 | VPOD1 | ($V_2O_5$ + iso-butanol + benzyl alcohol + Reflux 4 h) + o-$H_3PO_4$ + $CeN_3O_9 \cdot 6H_2O$ (Reflux 4 h) |
| VPPD2 | VPOD2 | ($V_2O_5$ + iso-butanol + benzyl alcohol + Reflux 6 h) + o-$H_3PO_4$ + $CeN_3O_9 \cdot 6H_2O$ (Reflux 2 h) |
| VPP | VPO | Conventional method ($V_2O_5$ + iso-butanol + benzyl alcohol + Reflux 7 h) + o-$H_3PO_4$ (Reflux 16 h) |

Example 2

The XRD analyses were carried out using a Shimadzu diffractometer model XRD 6000 employing $CuK_\alpha$ radiation to generate diffraction patterns from powder crystalline samples at ambient temperature. The total surface area and porosity of the catalysts were measured by the BET (Brunauer-Emmer-Teller) method using nitrogen adsorption at 77 K. This was done by the Sorptomatic 1990 series nitrogen adsorption/desorption analyzer.

Redox titration was carried out using the method of Niwa and Murakami to estimate the average oxidation number to vanadium.

The XRD patterns of the conventional VPO and precursors obtained by new organic method, as shown in FIG. 1, gave only the characteristic reflections of vanadyl hydrogen phosphate hemihydrate, $VOHPO_4 \cdot 0.5H_2O$ with the main reflections that appeared at 2θ=15.5°, 19.7°, 24.2°, 27.1°, 28.7°, 30.4°, 37.5° and 49.2° corresponding to (0 0 1), (1 0 1), (0 2 1), (1 2 1), (2 0 1), (1 3 0), (0 4 0) and (3 3 1) planes, respectively.

Figure 2:
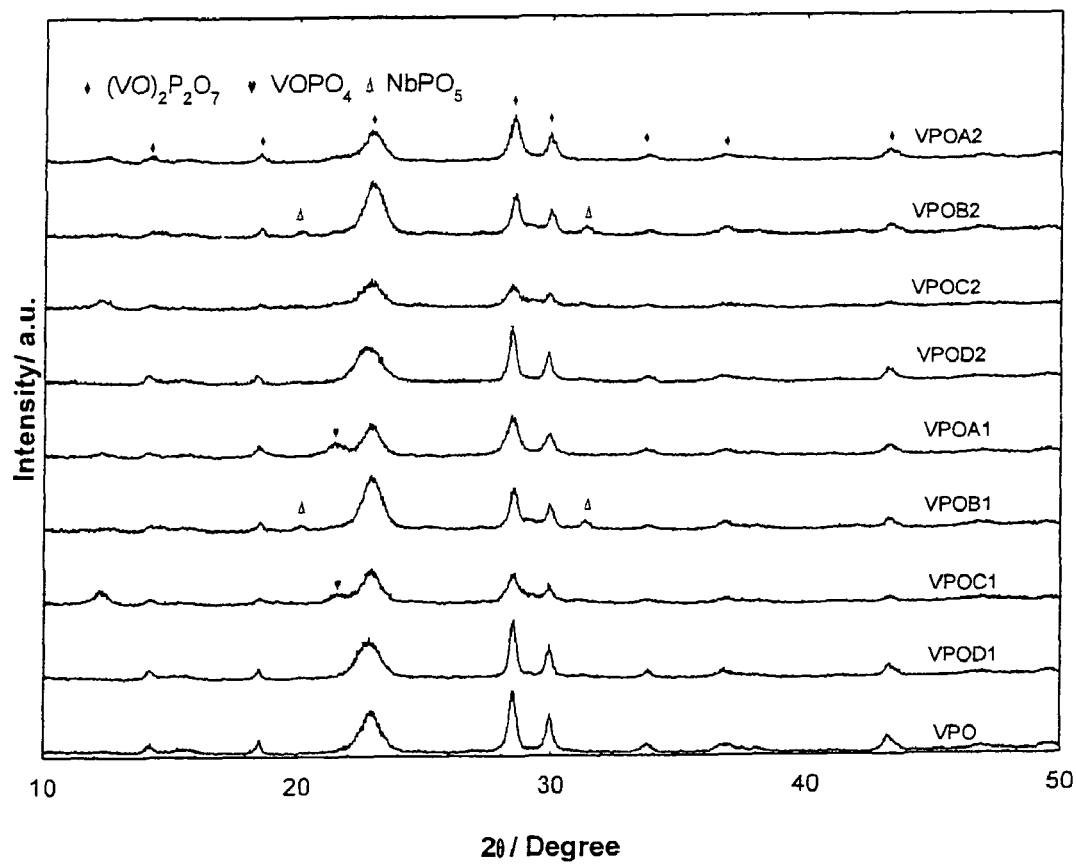
FIG. 2 XRD Patterns of the new and conventional VPO method for doped and undoped of vanadium phosphate catalyst catalysts; (020) and (204) main peaks for $(VO)_2P_2O_7$.

The $(VO)_2P_2O_7$ phase (JCPDS File No. 34-1381) shown in FIG. 2 gave main peaks at 2θ=22.6°, 28.2° and 29.7° which correspond to (0 2 0), (2 0 4) and (2 2 1) reflections, respectively. As to VPOA1 and VPOC1 catalysts, which was prepared by new method, $VOPO_4$ phase (JCPDS File No. 27-0948) was the only other phase accompany with $(VO)_2P_2O_7$ phase. $NbPO_5$ was also observed (JCPDS File No. 27-1316) together with and $(VO)_2P_2O_7$ as the main phase when VPO was intermingled with Nb.

Furthermore, Table 3 indicates that the values of the full width at half maximum (FWHM) were increased, i.e. from 0.493° (conventional) to 0.795° and 0.845° for the new reflux time of 4 and 6 h, respectively, along the (0 2 0) plane and from 0.377° (conventional) to 0.613° for the new reflux time of 4 h, along the (2 0 4) plane. However, a further reflux to 6 h refluxed, the values of FWHM to 0.558° along the (2 0 4) plane. By using the Debye-Scherrer equation, it was found that the crystallite size of the catalysts was reduced by using this new method, i.e. from 16.25 nm (conventional) to 10.08 nm and 9.48 for the new reflux time of 4 and 6 h, respectively, along the (0 2 0) plane and from 21.48 nm (conventional) to 13.27 nm and 14.53 for the new reflux time of 4 and 6 h, respectively, along the (2 0 4) plane. In addition, the development of this new preparation method also led to an increment in the values of $I_{(0\ 2\ 0)}/I_{(2\ 0\ 4)}$, indicating that a higher exposure of (0 2 0) plane was increased which contained the vanadyl group. Previous literatures reported that the best effect in the improvement of catalytic performance can be reached by an increase in the relative exposure of (0 2 0) plane of the $(VO)_2P_2O_7$ because this plane is involved in the reaction of partial oxidation of n-butane to MA. However, there is different between the active VPO catalyst prepared which is used new and conventional method for the treatment of precursors. It is clear that the catalysts that are prepared by this new method produced much smaller crystallite size (Table 3). This is consistent with the surface areas of these materials, which were determined by nitrogen adsorption according to the BET method (Table 2). Table 2 shows the effect of the preparation condition on the BET surface area, oxidation state of vanadium as well as percentage of $V^{4+}$ and $V^{5+}$ presence in the catalysts. The specific surface area of the catalysts, which is used new method, was significantly larger than that of the catalysts obtained by conventional VPO method, as shown in Table 2.

TABLE 2

| | Surface area | Oxidation state of vanadium | | |
|---|---|---|---|---|
| Catalyst | ($m^2g^{-1}$) | $V^{5+}$(%) | $V^{4+}$(%) | Average |
| VPOA1 | 28 | 12 | 88 | 4.12 |
| VPOA2 | 35 | 14 | 86 | 4.14 |
| VPOB1 | 40 | 4.0 | 96 | 4.04 |
| VPOB2 | 58 | 14 | 86 | 4.14 |
| VPOC1 | 44 | 16 | 84 | 4.16 |
| VPOC2 | 66 | 27 | 73 | 4.27 |
| VPOD1 | 47 | 15 | 85 | 4.15 |
| VPOD2 | 50 | 17 | 83 | 4.17 |
| VPO | 21 | 30 | 70 | 4.30 |

The surface area for undoped and 4 h reflux in first step (VPOA1) catalysts increased from 21 $m^2g^{-1}$ (conventional VPO method) to 28 $m^2g^{-1}$ and then further increased to 35 $m^2g^{-1}$ after 6 h refluxed (VPOA2).

The specific area of doped catalyst VPOB1, VPOC1, VPOD1 and VPOD2 was almost was two times of that of conventional VPO catalyst with the highest achieved by VPOB2 and VPOC2 with 58 and 66 $m^2g^{-1}$, respectively.

Figure 3A:
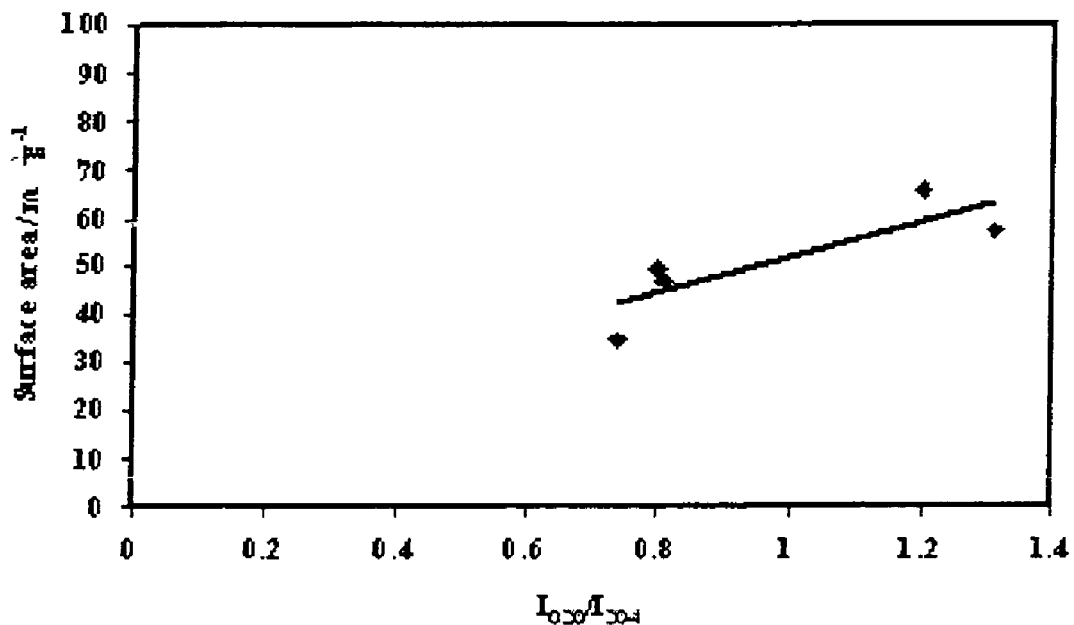
FIG. 3 shows the relation between (a) surface area and $I_{020}/I_{204}$, (b) surface area and crystallite size (020) phase of vanadium phosphate catalyst prepared by new and conventional VPO method.
Figure 3B:
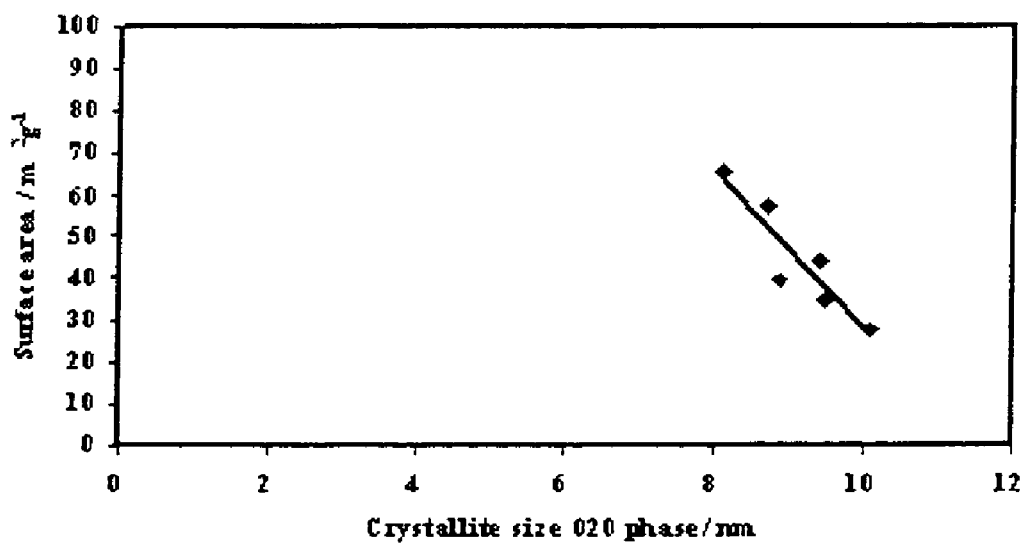

These values were significantly higher then those reported earlier for VPO catalyst prepared via conventional aqueous, organic, dihydrate and hydrothermal method. At present, most approaches for the synthesis of large-surface-area, high-activity catalysts make use of organic media; especially when the amount of water in solution is controlled. Water, aldehyde and ketone forms as an alcohol reduction product, but their amount can control by extractive distillation during the synthesis of the precursor phase. Water based preparations tend to lead to low-surface area materials. Correlation between crystallite size (020) phase and $I_{020}/I_{204}$ with surface area of the catalysts (FIG. 3) has shown that the crystallite size for undoped and 4 h reflux in it step (VPOA1) catalysts reduce from 16.25 nm (conventional VPO method) to 10.08 nm and then further decreasing to 9.48 nm after 6 h reflux (VPOA2). However, the crystallite size of doped catalyst VPOB1, VPOB2, VPOC2 and VPOD1 was almost two times lower than the conventional organic method synthesized VPO catalyst (Table 3).

The first key point with respect to vanadium phosphate catalysts, namely that the surface area is the factor that controls the activity of catalyst. The active catalyst has linear relationship between n-butane conversions with the catalyst surface area. This implies that the surface structure of the activated catalysts are very similar and the activity differences are just due to the higher surface area VPO catalyst having a higher number of active sites per unit mass of catalyst. A particular advantage of higher surface area catalysts is that they can be operated at lower temperatures which leads to an enhanced selectivity and hence yield in product being obtained. The surface area for undoped and 4 h reflux in first step (VPOA1) catalysts increased from 21 $m^2g^{-1}$ (conventional VPO method) to 28 $m^2g^{-1}$ and then further increased to 35 $m^2g^{-1}$ after 6 h refluxed (VPOA2).

The average vanadium oxidation number of the material that was reflux for 4 h (VPOA1) was found to be 4.12 compared to the conventional (4.30) and further increased to 4.14 for 6 h reflux (VPOA2). This was due to an increment of $V^{4+}$ oxidation state from 70% to 86%. However, the amount of the $V^{4+}$ was increased to 96%, corresponding to a decrease in the average vanadium oxidation state to 4.04 for the Nb doped catalyst, which is refluxed for 4 h (VPOB1). As shown, for all precursors are prepared by new method, the amount of $V^{4+}$ was slightly increased as compared to conventional VPO route.

TABLE 3

| Catalysts | $I_{(020)}/I_{(204)}$[a] | FWHM[b] ( ) (020) | (204) | Crystallite size[c] (nm) (020) | (204) |
|---|---|---|---|---|---|
| VPOA1 | 0.83 | 0.7950 | 0.6109 | 10.08 | 13.27 |
| VPOA2 | 0.74 | 0.8450 | 0.5577 | 9.48 | 14.53 |
| VPOB1 | 1.52 | 0.9060 | 0.5296 | 8.85 | 15.30 |
| VPOB2 | 1.31 | 0.9224 | 0.4696 | 8.68 | 17.25 |
| VPOC1 | 1.24 | 0.8533 | 0.6700 | 9.39 | 12.10 |
| VPOC2 | 1.20 | 0.9900 | 0.6487 | 8.08 | 12.49 |
| VPOD1 | 0.81 | 1.0600 | 0.4737 | 7.56 | 17.11 |

TABLE 3-continued

| Catalysts | $I_{(020)}/I_{(204)}$[a] | FWHM[b] ( ) (020) | (204) | Crystallite size[c] (nm) (020) | (204) |
|---|---|---|---|---|---|
| VPOD2 | 0.80 | 1.1580 | 0.4685 | 6.92 | 17.09 |
| VPO | 0.24 | 0.4932 | 0.3774 | 16.25 | 21.48 |

[a]Ratios of relative peak intensities
[b]Full width at half maximum.
[c]Plate thickness by means of Scherrer's formula: T( ) = (0.89 × λ)/(FWHM × cos θ).

Example 3

The surface morphology of the catalysts was observed under a scanning electron microscope, using a LEO operated at accelerating voltages of 15 kV. The samples suitable for SEM were prepared by dispersing the catalyst powder on a metallic sample holder and glued them by using a double-sided tape. The samples were coated with a thin layer of gold which is a type of conducting materials using BIO-RAS Sputter Coater. Micrographs were recorded at various magnifications.

Figure 4:
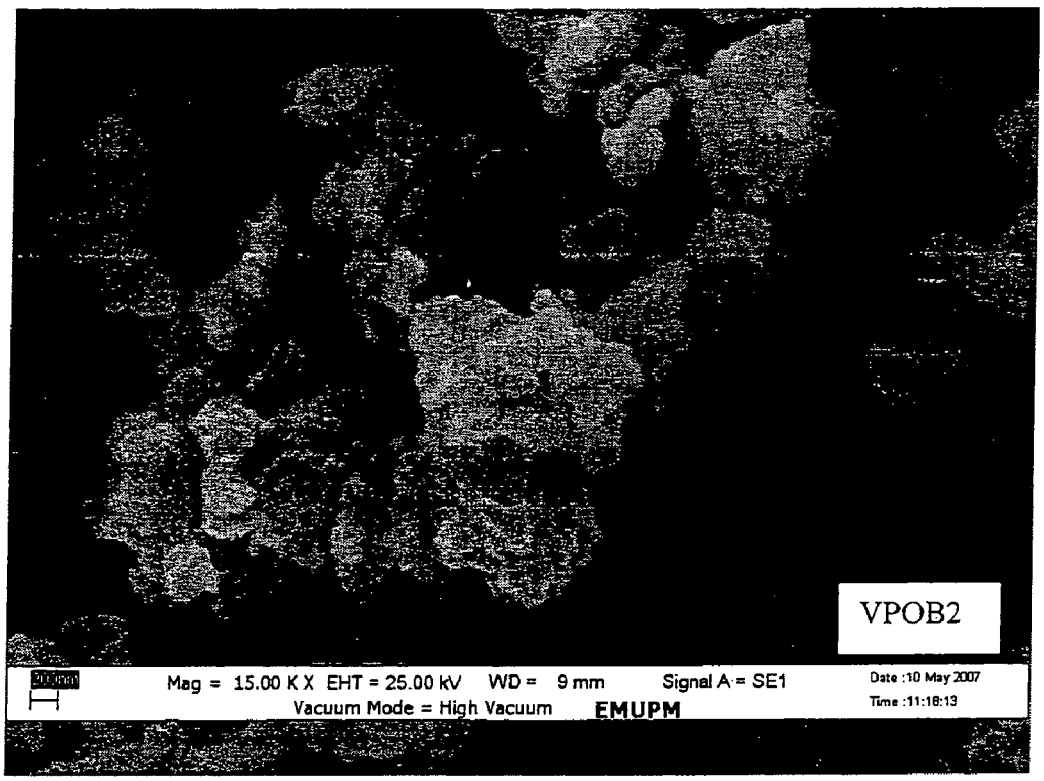
FIG. 4 is a scanning electron micrograph of the new method Nb doped catalyst.

SEM images revealed the morphologies of the samples (FIG. 4). VPOB2 showed nano-structure with a secondary structure of primary platelets of below 200 nm mean diameter (FIG. 4a). The small rounded particles white spots represent $NbPO_5$ particles mixed with VPO particles, they can be assigned to $NbPO_5$ particles as confirmed by XRD. The surface morphologies of VPOC2 catalysts provide shear forces which allowed the crystal platelets to slide away from one another, thereby exposing more surface plane (FIG. 4b). SEM of VPOD2 reveal, that the nano-structured sample obtained in the form of small particles and different size aggregated in a concentric secondary structure (FIG. 4c).

Comparing the series of the catalysts allows us to conclude that this new method produce the same mesoscopic state of secondary platelets made from sub-nanometer sized primary round platelets. These observations may explain the reason for a markedly increase in the surface area.

Example 4

Temperature-programmed reduction ($H_2$-TPR) in $H_2$/Ar experiment was performed using a Thermo Finnigan TPDRO 1100 apparatus provided with a thermal conductivity detector. The $H_2$-TPR analysis of fresh catalysts was done in $H_2$/Ar stream (5% $H_2$, 1 bar, 25 $cm^3$ $min^{-1}$) with raising the temperature from ambient to 1173 K at 5 K $min^{-1}$.

Figure 5:
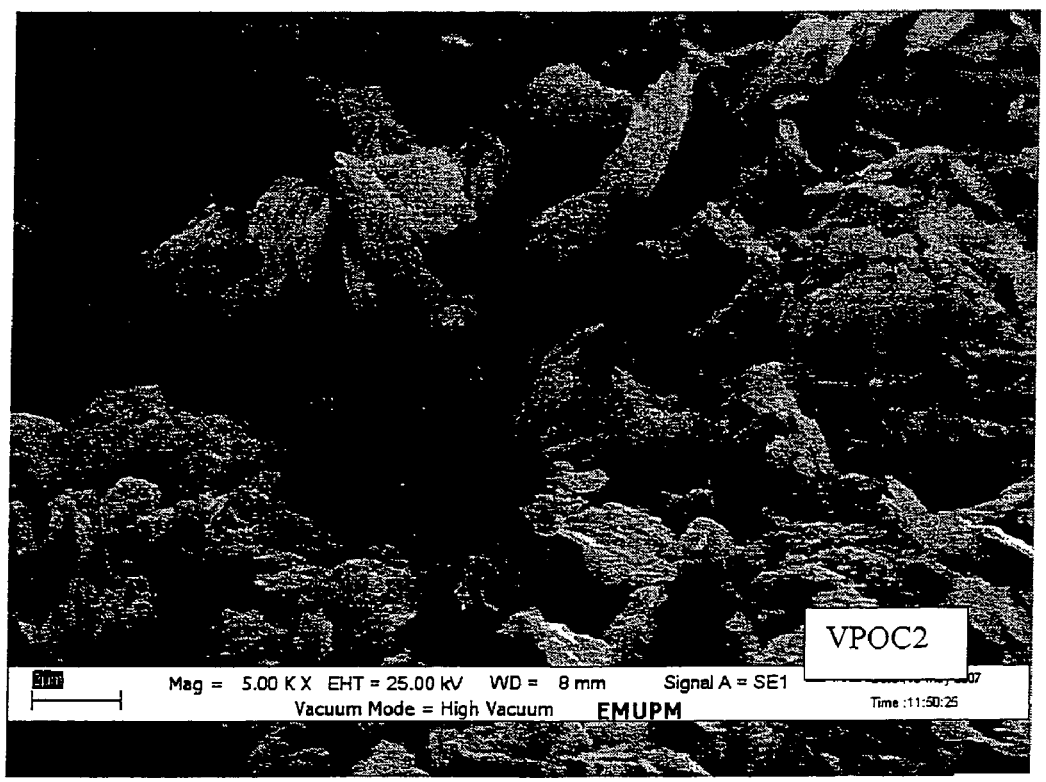
FIG. 5 is a scanning electron micrograph of the new method La doped catalyst.
Figure 6:
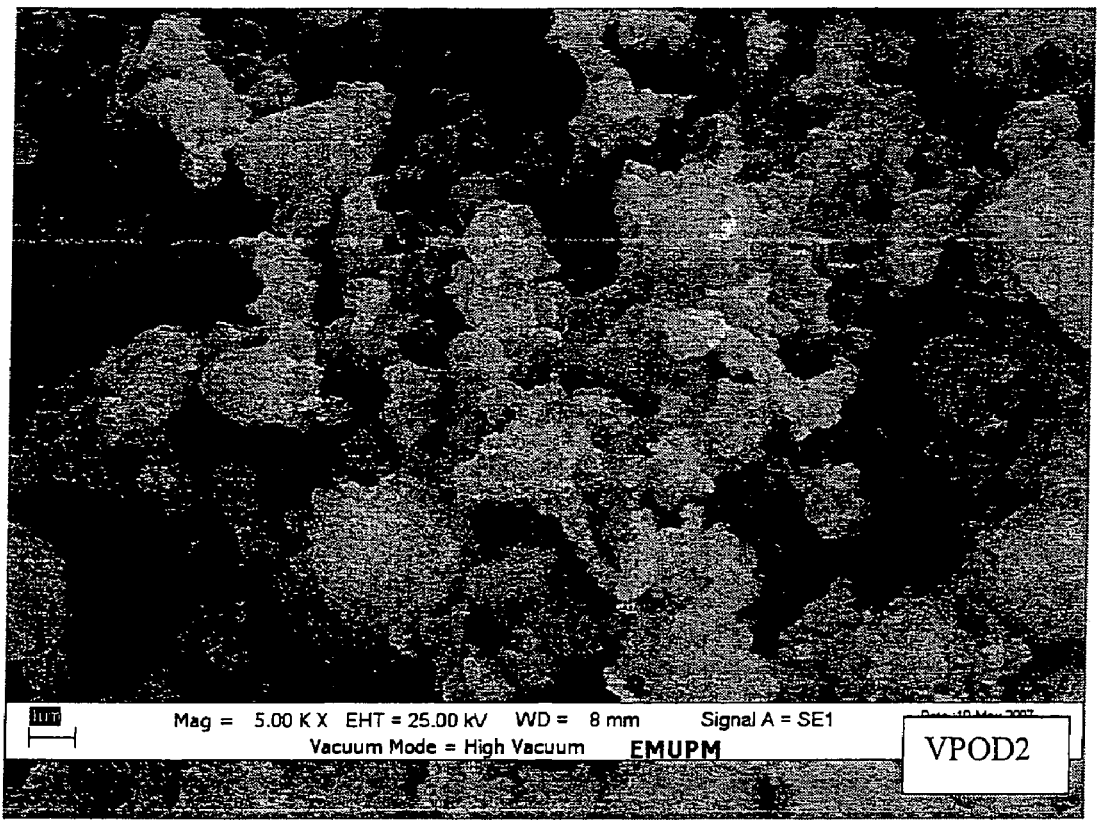
FIG. 6 is a scanning electron micrograph of the new method Ce doped catalyst.
Figure 7:
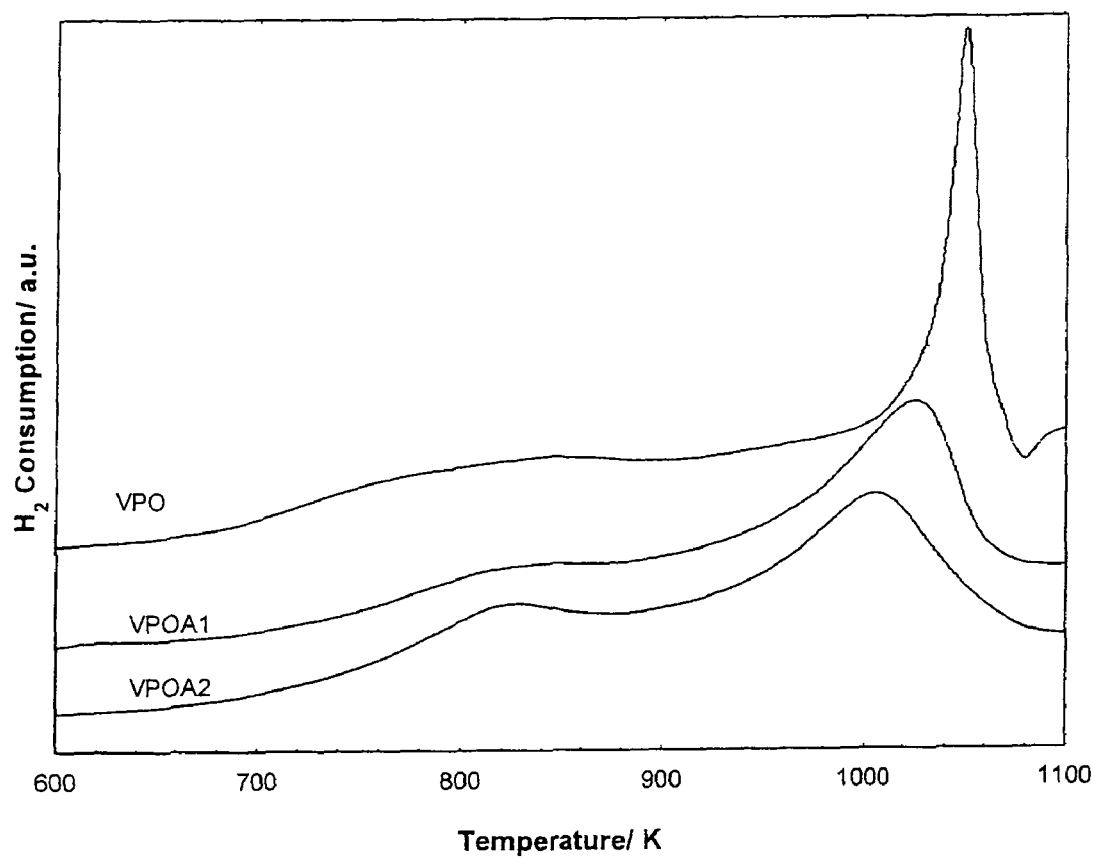
FIG. 7 shows the TPR Profiles of VPO catalysts prepared by conventional and new method.
Figure 8:
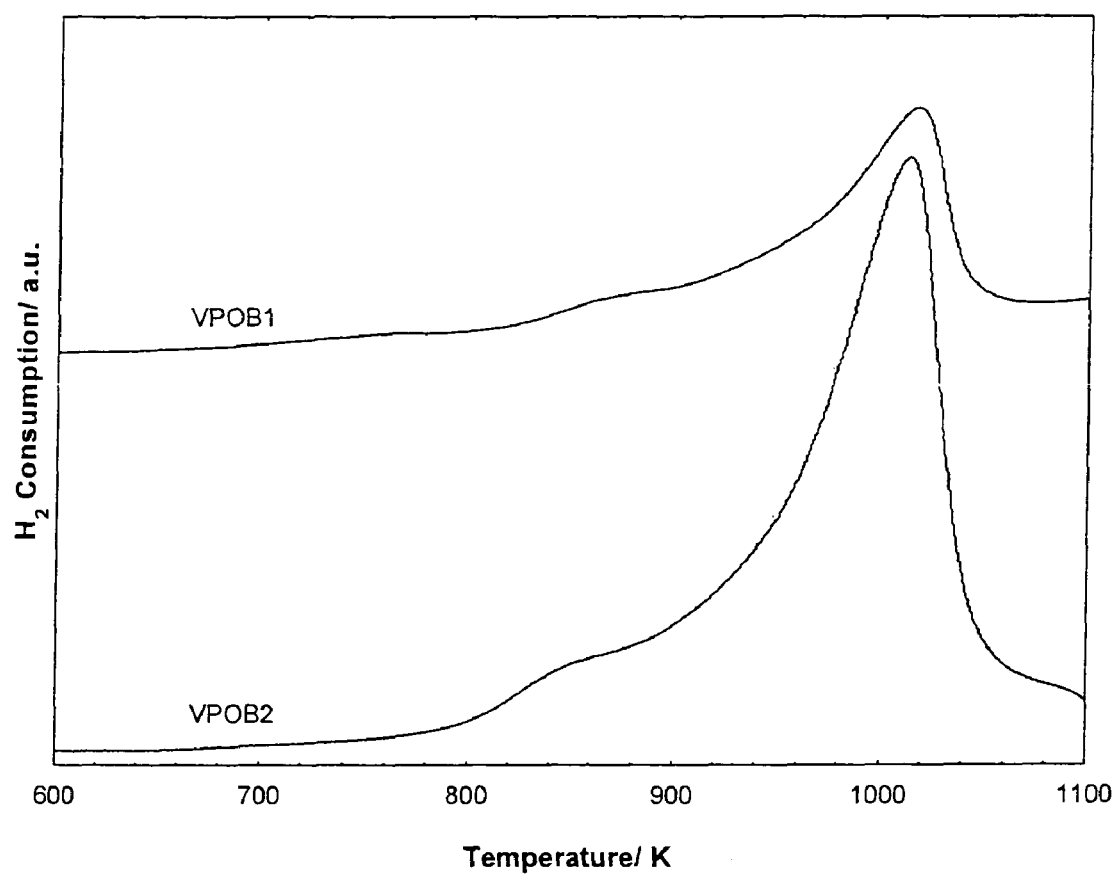
FIG. 8 shows the TPR Profiles of Nb doped VPO catalysts prepared by two new condition methods.
Figure 9:
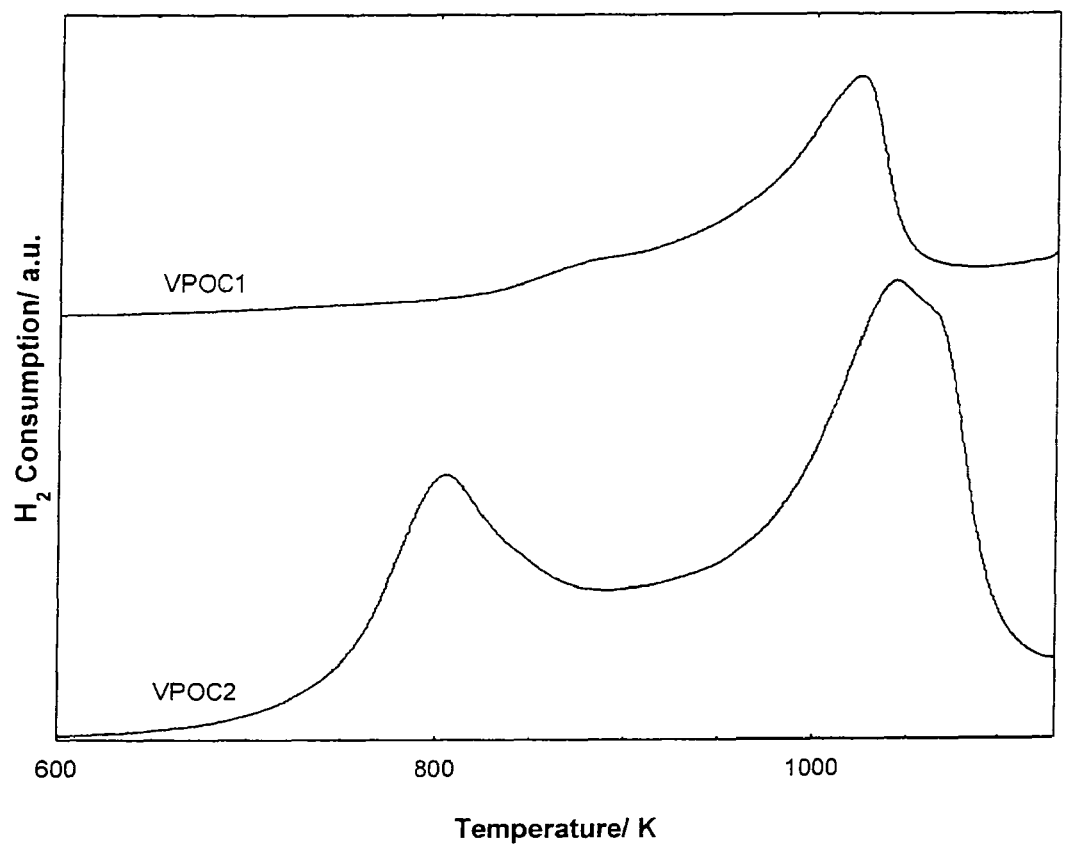
FIG. 9 shows the TPR Profiles of La doped VPO catalysts prepared by two new condition methods.
Figure 10:
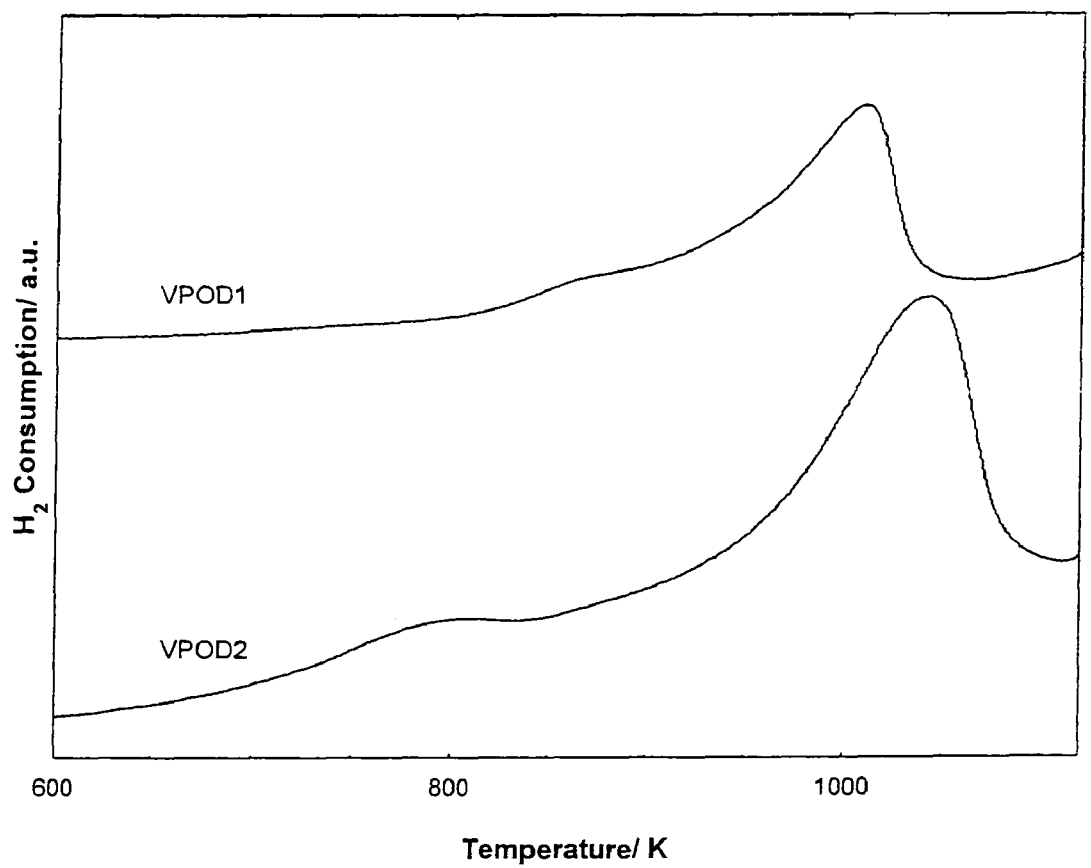
FIG. 10 shows the TPR Profiles of Ce doped VPO catalysts prepared by two new condition methods.
Figure 11:
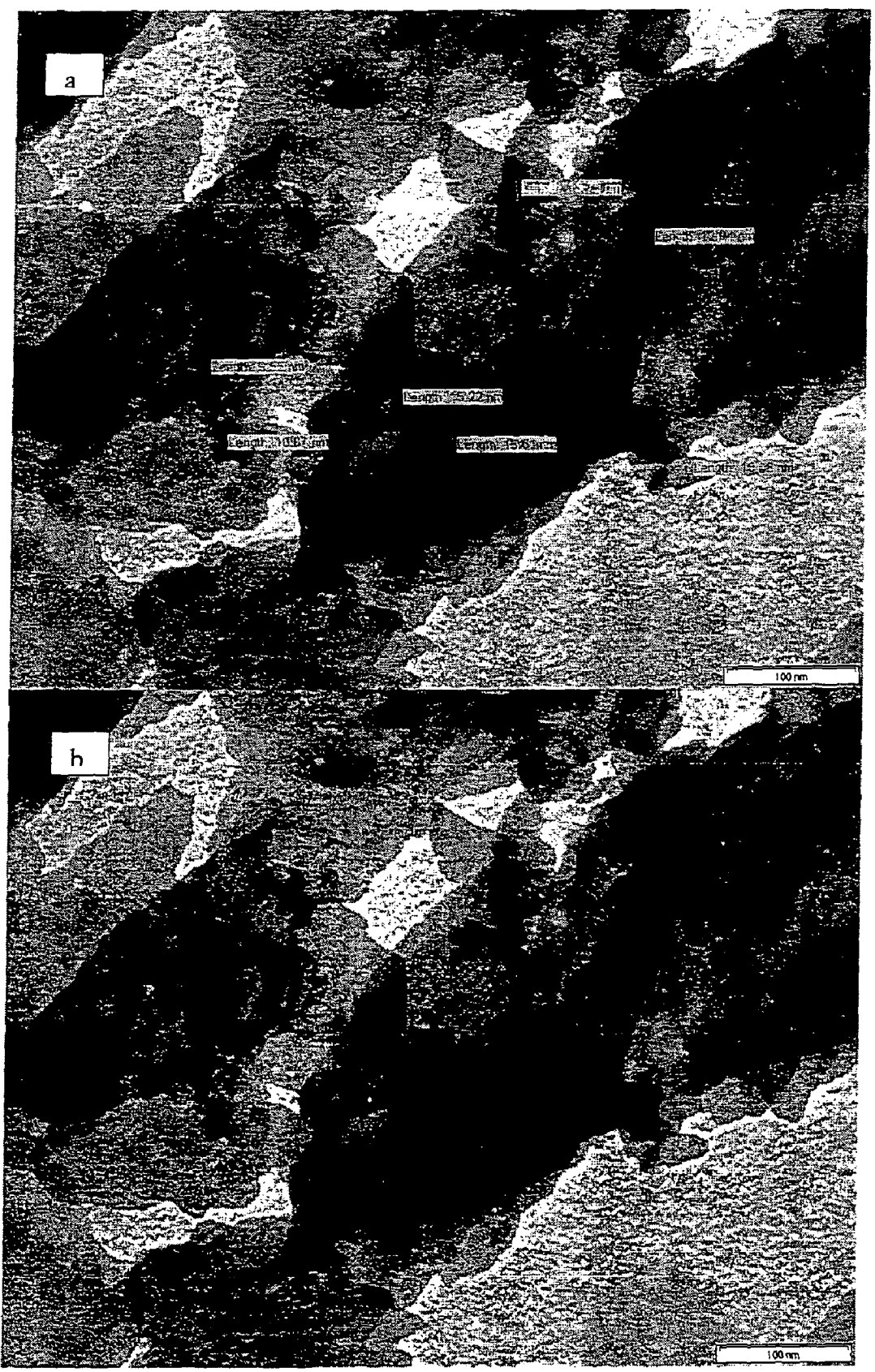
FIG. 11 shows the TEM images of VPOA2 catalysts.
Figure 12:
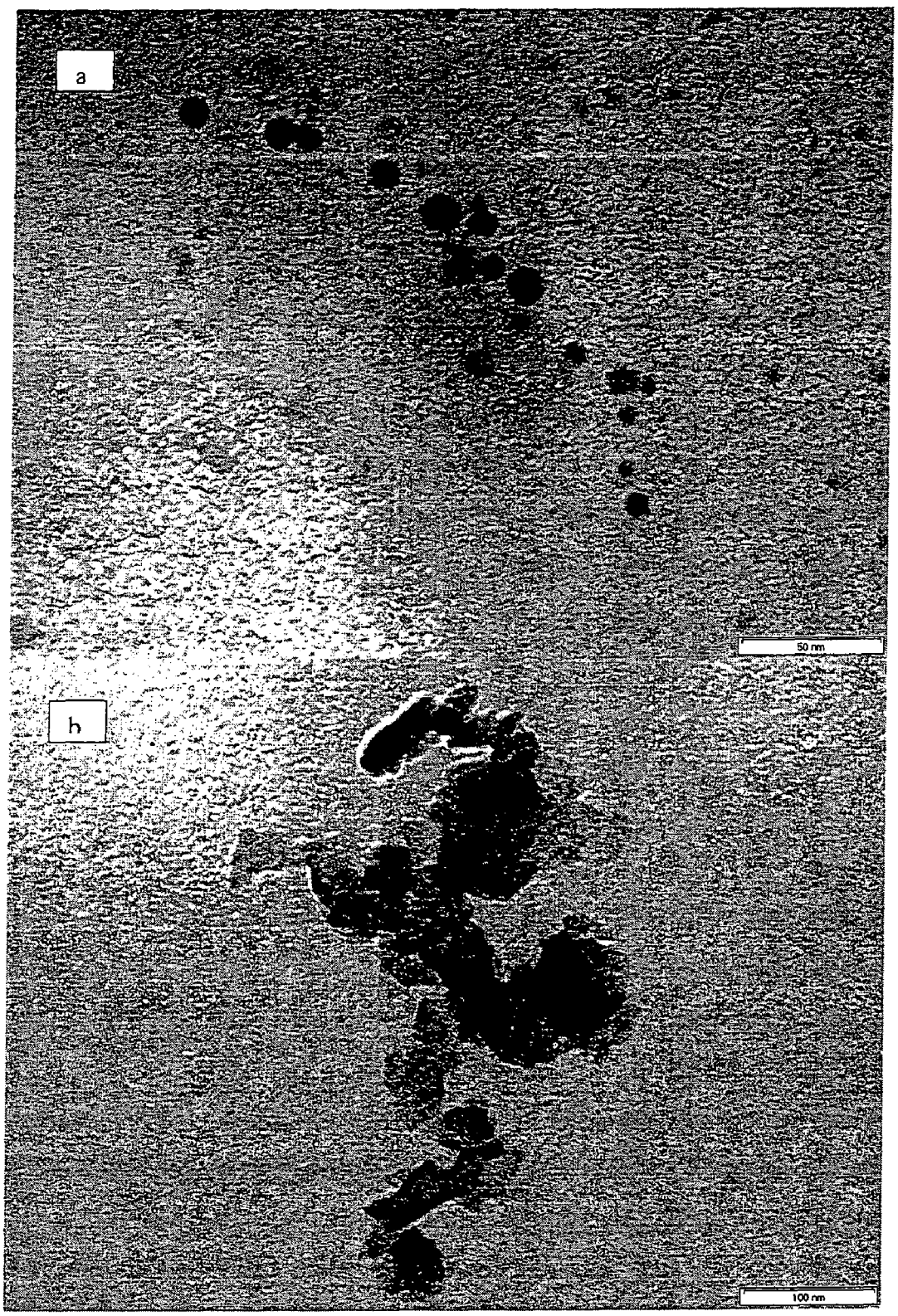
FIG. 12 shows the TEM images of VPOB1 catalysts.
Figure 13:
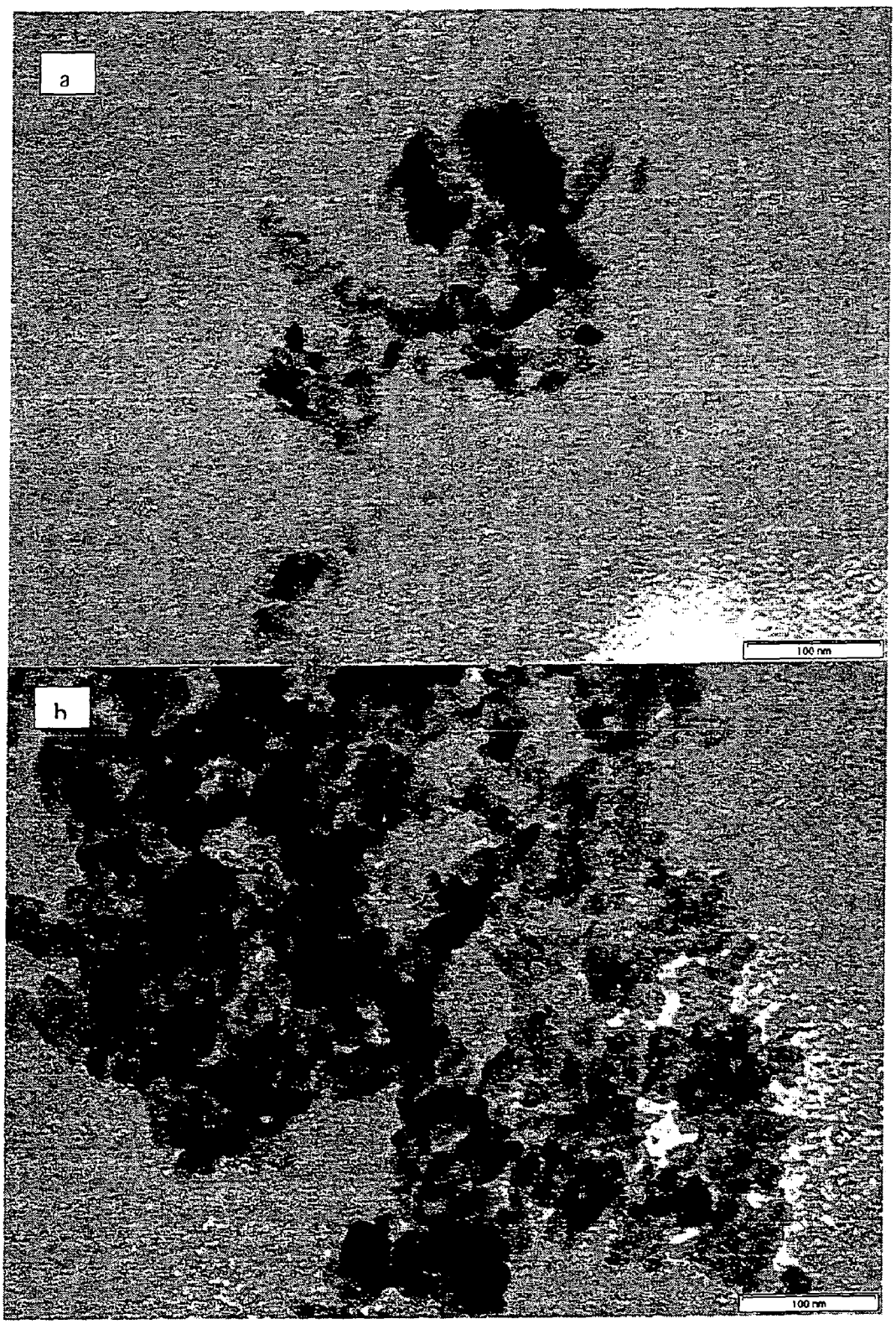
FIG. 13 shows the TEM images of VPOB2 catalysts.
Figure 14:
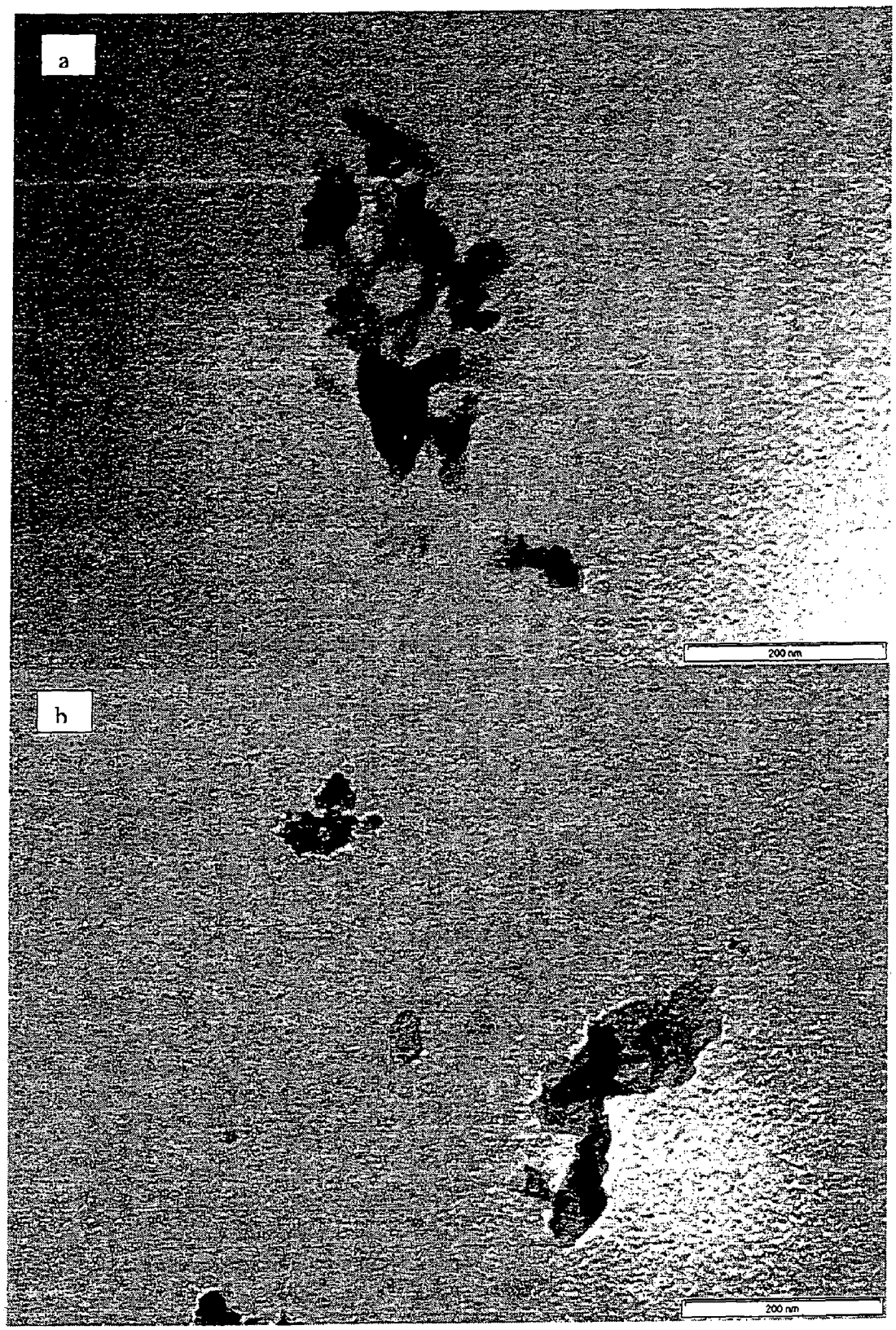
FIG. 14 shows the TEM images of VPOC1 catalysts.
Figure 15:
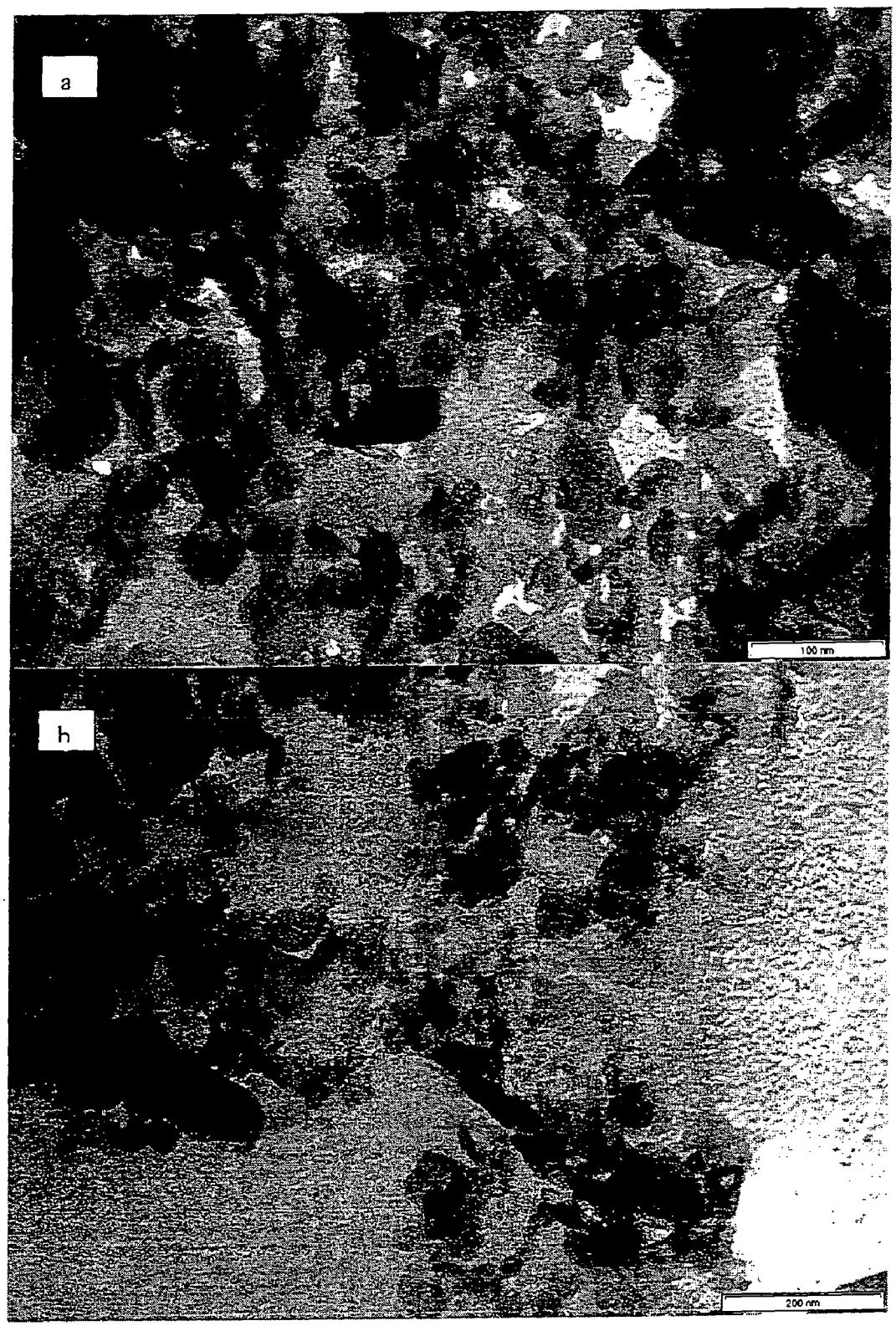
FIG. 15 shows the TEM images of VPOC2 catalysts.
Figure 16:
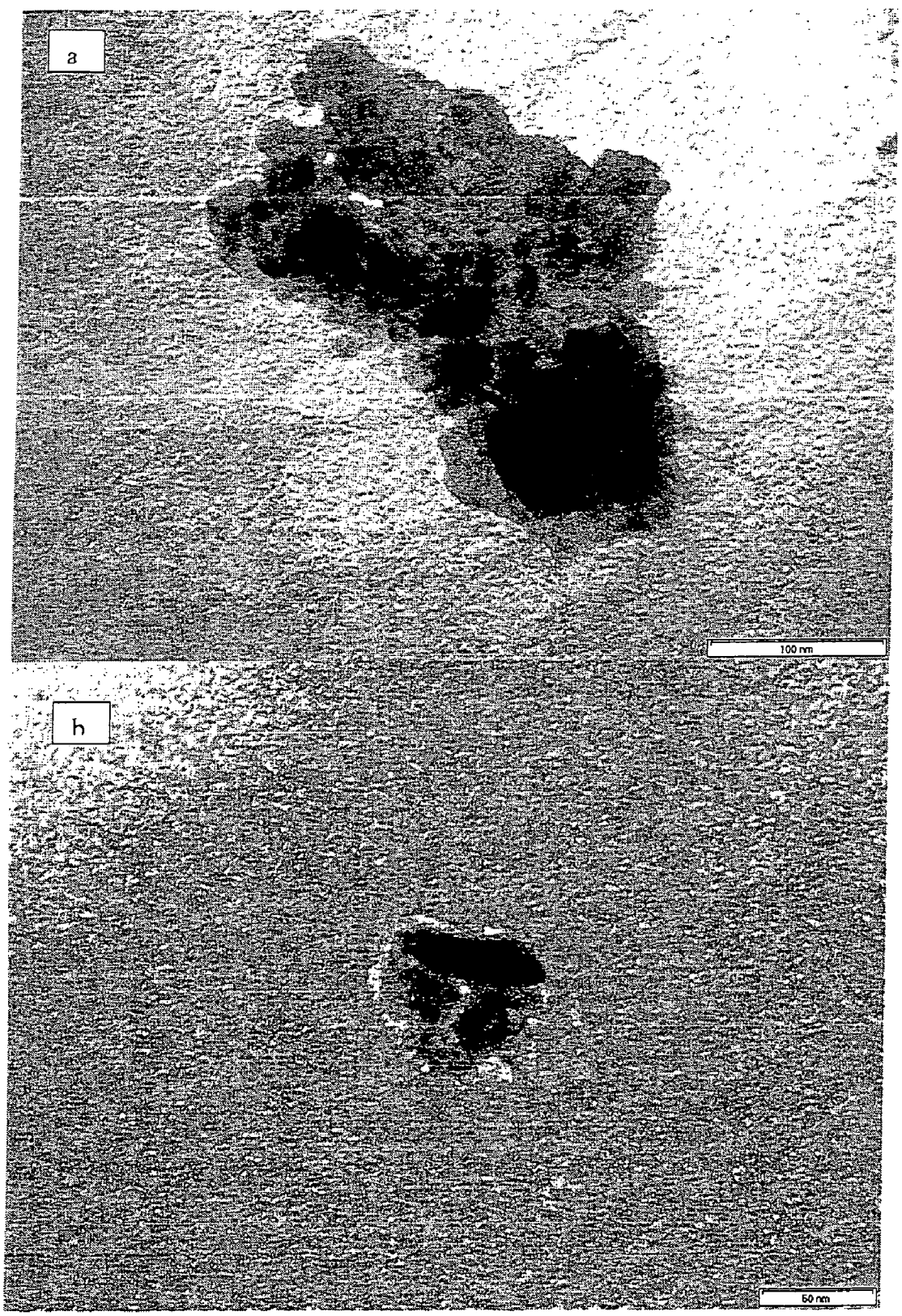
FIG. 16 shows the TEM images of VPOD1 catalysts.
Figure 17:
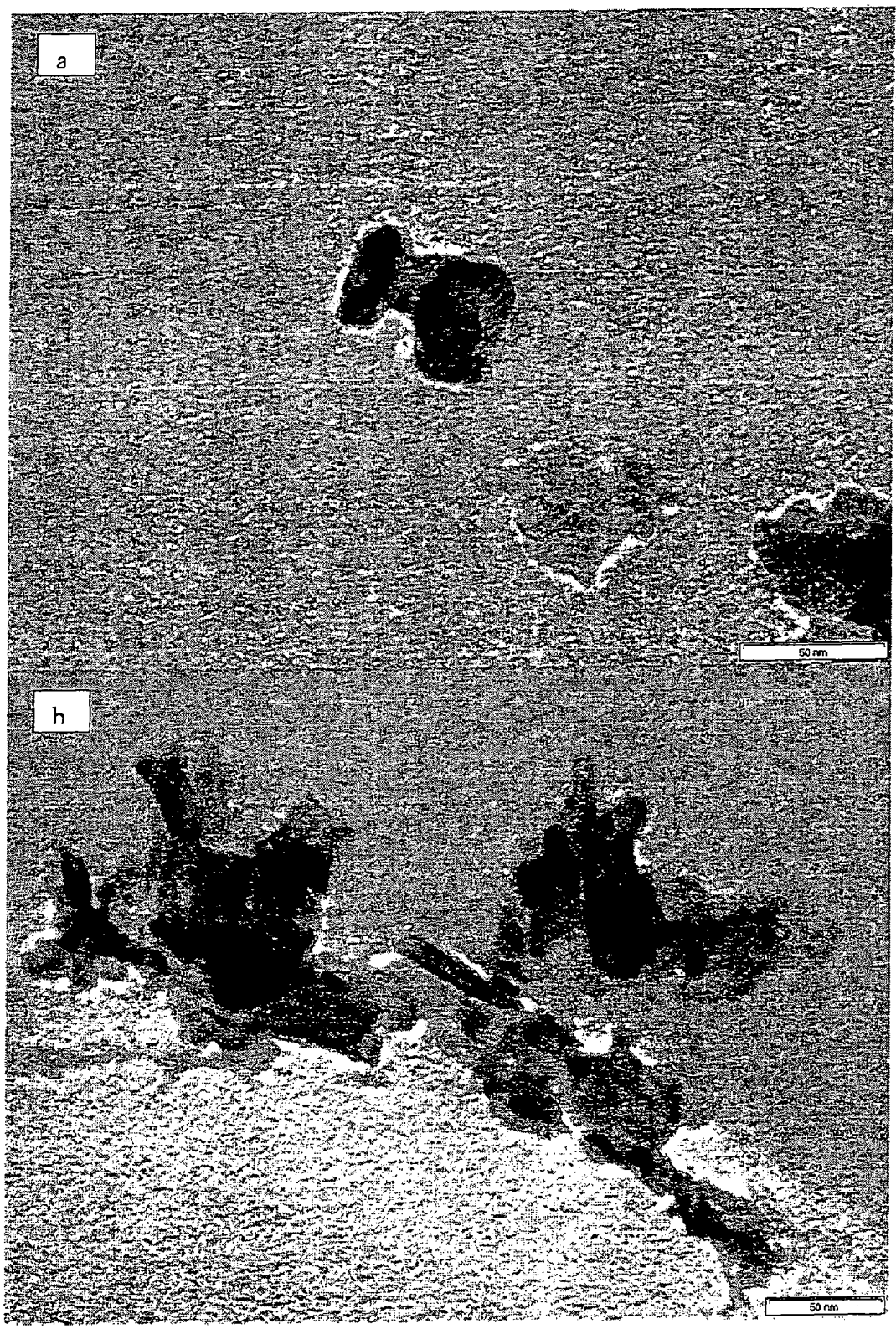
FIG. 17 shows the TEM images of VPOD2 catalysts.

In order to investigate the effect of preparation condition on the redox properties, amount and nature of the oxygen species of the catalysts, $H_2$-TPR experiments were performed on the conventional and new catalysts. FIG. 5 shows the profiles of $H_2$-TPR, and total amount of oxygen removed are shown in Table 4.

TABLE 4

| Catalysts | Peak | $T_{max}$ (K) | Reduction Activation Energy, Er (kJmol$^{-1}$) | Oxygen Atoms Removed (mol g$^{-1}$) × 10$^{-3}$ | Oxygen Atoms Removed (atom g$^{-1}$) × 10$^{21}$ | Ratio for Oxygen Removed of $V^{5+}/V^{4+}$ |
|---|---|---|---|---|---|---|
| VPOA1 | 1 | 841 | 140.4 | 0.311 | 0.19 | 0.34 |
|  | 2 | 1025 | 171.1 | 0.918 | 0.55 |  |
| Total oxygen atoms removed |  |  |  | 1.23 | 0.74 |  |
| VPOA2 | 1 | 826 | 137.9 | 0.71 | 0.43 | 0.5 |
|  | 2 | 1005 | 167.8 | 1.42 | 0.86 |  |
| Total oxygen atoms removed |  |  |  | 2.13 | 1.29 |  |

TABLE 4-continued

| Catalysts | Peak | $T_{max}$ (K) | Reduction Activation Energy, Er (kJmol$^{-1}$) | Oxygen Atoms Removed (mol g$^{-1}$) × 10$^{-3}$ | Oxygen Atoms Removed (atom g$^{-1}$) × 10$^{21}$ | Ratio for Oxygen Removed of $V^{5+}/V^{4+}$ |
|---|---|---|---|---|---|---|
| VPOB1 | 1 | 760 | 126.9 | 0.032 | 0.02 | 0.14 |
|  | 2 | 890 | 148.6 | 0.16 | 0.1 |  |
|  | 3 | 1016 | 169.6 | 1.39 | 0.83 |  |
| Total oxygen atoms removed |  |  |  | 1.58 | 0.95 |  |
| VPOB2 | 1 | 894 | 149.2 | 0.45 | 0.27 | 0.14 |
|  | 2 | 1012 | 168.9 | 3.304 | 1.99 |  |
| Total oxygen atoms removed |  |  |  | 3.75 | 2.26 |  |
| VPOC1 | 1 | 904 | 150.9 | 0.15 | 0.09 | 0.12 |
|  | 2 | 1024 | 170.9 | 1.28 | 0.77 |  |
| Total oxygen atoms removed |  |  |  | 1.43 | 0.86 |  |
| VPOC2 | 1 | 804 | 134.2 | 1.72 | 1.04 | 0.56 |
|  | 2 | 1044 | 174.3 | 3.08 | 1.86 |  |
| Total oxygen atoms removed |  |  |  | 4.8 | 2.9 |  |
| VPOD1 | 1 | 866 | 144.6 | 0.15 | 0.09 | 0.11 |
|  | 2 | 1009 | 168.4 | 1.3 | 0.78 |  |
| Total oxygen atoms removed |  |  |  | 1.45 | 0.87 |  |
| VPOD2 | 1 | 791 | 132 | 0.21 | 0.13 | 0.14 |
|  | 2 | 1042 | 173.9 | 1.51 | 0.91 |  |
| Total oxygen atoms removed |  |  |  | 1.72 | 1.04 |  |
| VPO | 1 | 840 | 140.2 | 0.37 | 0.22 | 0.43 |
|  | 2 | 1050 | 175.3 | 0.85 | 0.51 |  |
| Total oxygen atoms removed |  |  |  | 1.22 | 0.73 |  |

The conventional catalyst gave characteristic two reduction peaks at 840 and 1050 K, where the first peak is the reduction of $V^{5+}$ phase whereas the second peak is assigned to the removal of lattice oxygen from the active $V^{4+}$ phase. The amount of oxygen removed from both peaks is $2.2 \times 10^{20}$ and $5.1 \times 10^{20}$ atom g$^{-1}$, respectively, with an oxygen ratio for $V^{5+}$ to $V^{4+}$ of 0.43. The new catalysts show similar reduction profiles to the conventional material. It was found that the 4 h refluxed catalyst (VPOA1) slightly decreased the temperature of the second peak decreased by 25 K. Nevertheless, 6 h refluxed catalyst (VPOA2) also showed shifts of both reduction peaks to lower temperatures, i.e. 826 and 1005 K. The amount of oxygen species released associated with $V^{5+}$ reduced to $1.9 \times 10^{20}$ atom g$^{-1}$ for 4 h refluxed catalyst. However, further refluxed to 6 h significantly increased the amount to $4.3 \times 10^{20}$ atom g$^{-1}$. The amount for oxygen species removed from the second reduction peak, which is attributed to the reduction of $V^{4+}$ decreased to $(5.5$ and $8.6) \times 10^{20}$ atom g$^{-1}$ for new refluxed time of 4 and 6 h, respectively. The oxygen atom released ratio of $V^{5+}$ to $V^{4+}$ for new method catalysts is 0.34 and 0.50 for refluxed time of 4 and 6 h, respectively. The results show that 6 h of refluxed which is the reduction of $V^{5+}$ to $V^{4+}$ phase in the synthesis procedure is the optimum duration to obtain a highly active catalyst as this catalyst possesses highest amount of active $V^{4+}$—O$^-$ pair for n-butane activation and an appropriate oxygen species ratio associated with $V^{5+}$ to $V^{4+}$. Interestingly, the incorporating of Nb and La dopants as for 6 h refluxed catalyst significantly increased the total amount of oxygen to 2.26 and $2.90 \times 10^{21}$ atom g$^{-1}$ with an increment of 30.9 and 39.7%, respectively. This, suggested that Nb and La dopants are highly potential as promoter for these vanadium phosphate catalysts.

Example 5

The TEM images were obtained in a Philips electron microscope. This instrument has been fitted with a TV camera and high resolution Slow Scan CCD camera. For this analysis, a suspension in ethanol was achieved by stirring the solid sample with ultrasound for 15 min. A few drops of the resulting suspension were deposited on a TEM grid (lacey carbon film supported on a copper 400 mesh) and subsequently dried and evacuated before the analysis. Individual frames from which images can be captured subsequently into a computer for enhancement and detailed analysis.

Transmission electron micrographs of typical and particle size from the VPO catalysts are shown in FIGS. 11 to 17 respectively. It is clear from the micrographs that the catalysts illustrated characteristic rhomboid platelet morphology.

In general, nanoparticles have a high surface area, and hence provide higher catalytic activity. Nanotechnologies are enabling changes in the degree of control in the production of nanoparticles, and the support structure on which they reside. This allows more uniformity in the size and chemical structure of the catalyst, which in turn leads to greater catalytic selectivity and activity and the production of fewer by-products. The lateral lengths and average particle size of the all catalysts were 10-100 and 40-60 nm, respectively. In the TEM images of the catalysts, monolithic particles were observed. In contrast, mosaic patterns were observed inside the particles of the doped and undoped catalysts, indicating that the particles of the catalysts were polycrystalline; the patterns different drastically depending on the catalyst. The particle of contained irregular shaped platelets, oblong and circles microcrystallites showing in its inside.

Example 6

The oxidation of n-butane to maleic anhydride was carried out in a fixed-bed flow microreactor containing a standard mass of catalyst (0.25 g) at 673 K with GHSV of 2400 h$^{-1}$.

Prior to use, the catalysts were pelleted and sieved to give particles (250-300 μm in diameter). n-Butane and air were fed to the reactor via calibrated mass flow controllers to give a feedstock composition of 1.7% n-butane in air. The products were fed via heated lines to an on-line gas chromatography for product analysis. The reactor comprised a stainless steel tube with the catalyst held in place by plugs of quartz wool. A thermocouple was located in the centre of the catalyst bed and temperature control was typically±1 K. Carbon mass balances of ≧95% were typically observed.

A significant improvement of the catalytic performance is observed for the n-butane conversion when the VPO catalyst was prepared by new method and 6 h refluxed. VPOC2 gave 84% of conversion (two fold) compared to only 42% for 4 h refluxed (VPOC1) (Table 5). The effect can be correlated with the increase of the BET area which connected to the development of (020) plane of $(VO)_2P_2O_7$. New method also leads to the reducibly behavior of the catalyst. Higher amount of active site ($V^{4+}$) the associated and oxygen species which responsible for the activation of n-butane also contributed to the enhancement of the activity. Furthermore, the smaller particle size at (020) plane obtained for the new method catalyst which tends contributed strongly to improve the MA selectivity.

TABLE 5

| Catalyst | n-Butane conversion (%) | Product selectivity (%) | | |
|---|---|---|---|---|
| | | MA | CO | CO2 |
| VPOC1 | 64 | 58 | 11 | 31 |
| VPOC2 | 35 | 53 | 12 | 35 |

$^a$Reaction conditions: 673 K, 1.7% n-butane in air, GHSV = 2400 h$^{-1}$.

The adoption of new method for preparation catalyst precursor in this study increased the full width at half maximum (FWHM) and reduced the crystallite size of the catalysts and consequently increased their surface area without affecting the principal phase structures of $VOHPO_4.0.5H_2O$ and $(VO)_2P_2O_7$.

Therefore with this new method having nanoparticle (50-100 nm) and consequently, significantly high surface area (>50 m$^2$g$^{-1}$) for VPO catalyst will provide a high active site for the reaction to be occurred. The active catalyst has linear relationship between light alkane conversions with the catalyst surface area.

In other hand, the present of nano-structured and prevent the crystal platelets the crystal platelets from tightly stacking together, thereby exposing more surface plane. The oxygen species of 6 h refluxed catalyst was found to be the most reactive with high amount of oxygen species (O$^-$) associated with the active $V^{4+}$ phase. The new method derived VPO catalyst ones exhibited higher reactivity for n-butane oxidation resulted in a higher removal of oxygen species associated with $V^{4+}$ phase and also some amount of oxygen species associated with $V^{5+}$ phase.

The invention claimed is:

1. A process to produce vanadyl hydrogen phosphate hemihydrates, comprising the steps of:
    (a) reducing vanadium-containing compounds in an alcohol solution selected from the group consisting of isobutanol, benzyl alcohol, and combinations thereof, under reflux for 4 to 6 hours to form a suspended mixture;
    (b) reacting dopants and phosphorus-containing compounds to the suspended mixture under reflux for 30 minutes to 3 hours to form the vanadyl hydrogen phosphate hemihydrate;
    (c) recovering the formed precursors from the suspended mixture; and
    (d) drying the recovered precursors via microwave irradiation.

2. A process according to claim 1, wherein the vanadium-containing compounds are selected from the group consisting of vanadium tetroxide, vanadium trioxide, vanadium pentoxide, vanadium halides, vanadium oxyhalides and combinations thereof.

3. A process according to claim 1, wherein the phosphorus-containing compounds are selected from the group consisting of metaphosphoric acid, orthophosphoric acid, triphosphoric acid, pyrophosphoric acid and combinations thereof.

4. A process according to claim 1, wherein the dopants are selected from the group consisting of Lanthanum (III) nitrate hexahydrate, Cerium (III) nitrate hexahydrate, Niobium Pentoxide and combinations thereof.

5. A process according to claim 1, wherein the ratio of the alcohol to vanadium atoms of the vanadium containing compounds is 20 to 40 by mL/g.

6. A process according to claim 1, wherein the ratio of vanadium atoms of the vanadium-containing compounds to phosphorus atoms of the phosphorus containing compounds is 0.053: 0.060 by mole.

7. A process according to claim 1, wherein ratio of the dopant to vanadium atoms of the vanadium-containing compounds is 0.01% to 0.04%.

8. A process according to claim 1, wherein ratio of the dopant to vanadium atoms of the vanadium-containing compounds is 0.01% to 0.04%.

9. A process according to claim 1, wherein the microwave irradiation is conducted at a frequency of 2450 MHz of 140 to 300 W.

10. A process to produce vanadium phosphorus oxide catalysts, comprising the steps of:
    (a) reducing vanadium-containing compounds in an alcohol solution selected from the group consisting of isobutanol and benzyl alcohol, and combinations thereof, under reflux for 4 to 6 hours to form a suspended mixture;
    (b) reacting dopants and phosphorus-containing compounds with the suspended mixture under reflux for 30 minutes to 3 hours to form precursors of the vanadium phosphorus oxide catalysts;
    (c) drying the formed precursors; and
    (d) calcining the dried precursors in a flow of gaseous hydrocarbon and air mixture at 400 to 460° C. to form activated vanadium phosphorus oxide catalysts, wherein the drying step is conducted by irradiating the formed precursor with microwave energy.

11. A process according to claim 10, wherein the vanadium-containing compounds are selected from the group consisting of vanadium tetroxide, vanadium trioxide, vanadium pentoxide, vanadium halides, vanadium oxyhalides, and combinations thereof.

12. A process according to claim 10, wherein the phosphorus-containing compounds are selected from the group consisting of metaphosphoric acid, orthophosphoric acid, triphosphoric acid, pyrophosphoric acid, and combinations thereof.

13. A process according to claim 10, wherein the dopants are selected from the group consisting of Lanthanum (III) nitrate hexahydrate, Cerium (III) nitrate hexahydrate, Niobium Pentoxide, and combinations thereof.

14. A process according to claim 10, wherein the ratio of the alcohol to vanadium atoms of the vanadium containing compounds is 20 to 40 by mL/g.

15. A process according to claim 10, wherein the ratio of vanadium atoms of the vanadium-containing compounds to phosphorus atoms of the phosphorus containing compounds is 0.053: 0.060 by mole.

16. A process according to claim 10, wherein the hydrocarbon is selected from the group consisting of propane, pentane, n-butane and combinations thereof.

17. A vanadium phosphorus oxide catalyst produced from a process according to claim 10, wherein the vanadium phosphorus oxide has a rhomboid platelet structure with an average particle size of 10-50 nm in width and 40-60 nm in length.

18. A process according to claim 10, wherein the microwave irradiation is conducted at a frequency of 2450 MHz of 140 to 300 W.

* * * * *